United States Patent
Pederson et al.

(10) Patent No.: US 6,215,019 B1
(45) Date of Patent: Apr. 10, 2001

(54) SYNTHESIS OF 5-DECENYL ACETATE AND OTHER PHEROMONE COMPONENTS

(75) Inventors: Richard L. Pederson, Bend, OR (US); Robert H. Grubbs, South Pasadena, CA (US)

(73) Assignee: TillieChem, Inc., San Gabriel, CA (US)

( * ) Notice: Subject to any disclaimer, the term of this patent is extended or adjusted under 35 U.S.C. 154(b) by 0 days.

(21) Appl. No.: 09/387,486

(22) Filed: Sep. 1, 1999

Related U.S. Application Data

(60) Provisional application No. 60/098,792, filed on Sep. 1, 1998.

(51) Int. Cl.$^7$ .................................................. C07C 67/02
(52) U.S. Cl. ........................................... 560/234; 560/261
(58) Field of Search ...................................... 560/234, 261

(56) References Cited

U.S. PATENT DOCUMENTS

| | | | |
|---|---|---|---|
| 4,844,916 | 7/1989 | Ogawa et al. | 424/409 |
| 4,923,119 | 5/1990 | Yamamoto et al. | 239/55 |
| 5,312,940 | 5/1994 | Grubbs et al. | 556/136 |
| 5,342,909 | 8/1994 | Grubbs et al. | 526/171 |
| 5,775,026 | 7/1998 | Pearce et al. | 43/124 |
| 5,916,983 | 6/1999 | Pederson et al. | 526/170 |

OTHER PUBLICATIONS

Couturier, J.L. et al., *Angew. Chem. Int. Ed. Engl.* (1992) 31, 628, "A Cyclometalated Aryloxy(chloro)neopentylidene-tungsten Complex: A Highly Active and Stereoselective Catalyst for the Metathesis of cis-and trans-2-Pentene, Norbornene, 1-Methyl-norbornene, and Ethyl Oleate".

J.W. Ellis et al. *Inorg. Chem.* (1992) 31, 3026–3033, "Water– Soluble Tris(hydroxymethyl)phosphine Complexes with Nickel, Palladium, and Platinum, Crystal Structure of [Pd{P(CH$_2$OH)$_3$}$_4$]•CH$_3$OH".

N.J. Goodwin et al., *Chem. Commun.* (1996) 1551, FcCH$_2$P(CH$_2$P(CH$_2$ OH)$_2$: a new, reactive yet air–stable ferrocene–derived phosphine [Fc=(η•C$_5$H$_5$)FeC$_5$H$_4$].

Grubbs et al., *Tetrahedron* (1998), 54, 4413–4450, "Recent Advances in Olefin Metathesis and Its Application in Organic Synthesis".

O'Leary,D.J. et al., *Tetrahedron Letters* (1998), 39, 7427, "A New Method for Cross–Metathesis of Terminal Olefins".

Scholl et al., *Organic Letters* (1999) 1, 953–956, "Synthesis and Activity of a New Generation of Ruthenium–Based Olefin Metathesis Catalysts Coordinated with 1,3–Dimesityl–4,5–dihydro–imidazol–2–ylidene Ligands".

*Primary Examiner*—Paul J. Killos
(74) *Attorney, Agent, or Firm*—Stoel Rives LLP

(57) ABSTRACT

The present invention relates to syntheses of 5-decenyl acetate, the major component in Peach Twig Borer pheromone, and other pheromone components. The syntheses entails few reaction steps, use commercially available starting materials, and have relatively short process times. A preferred embodiment of the syntheses involves self-metathesizing 1-hexene in the presence of Grubbs' catalyst, [(PCy$_3$)$_2$Cl$_2$]Ru=CHPh. The resulting 5-decene is then reacted with an alcohol or acetate protected hexene under vacuum to yield 5-decenyl acetate. These syntheses produce good yields without the need for expensive or sophisticated equipment.

26 Claims, 8 Drawing Sheets

Catalyst 2

FIG. 4B

Area Percent Report

Sorted By: Signal
Multiplier: 1.0000
Dilution: 1.0000

Signal 1: FID1 B,

| Peak # | RetTime [min] | Type | Width [min] | Area counts*s | Height [counts] | Area % |
|---|---|---|---|---|---|---|
| 1 | 1.767 | VV | 0.0228 | 1.12559e4 | 7813.26953 | 0.24205 |
| 2 | 1.833 | VV | 0.0240 | 5786.80859 | 3742.20679 | 0.12444 |
| 3 | 1.976 | VBA | 0.0400 | 5116.63184 | 1986.90942 | 0.11003 |
| 4 | 2.352 | BP | 0.0258 | 3418.63306 | 2244.88330 | 0.07352 |
| 5 | 2.516 | VP | 0.0294 | 1.33072e4 | 6640.63281 | 0.28616 |
| 6 | 4.329 | PV | 0.0400 | 4.48158e4 | 1.74463e4 | 0.96373 |
| 7 | 4.483 | VB | 0.0416 | 9248.50977 | 3412.45703 | 0.19888 |
| 8 | 6.095 | PV | 0.0702 | 2.26914e6 | 4.55085e5 | 48.79635 |
| 9 | 6.186 | VB | 0.0354 | 4.65956e5 | 1.98460e5 | 10.02006 |
| 10 | 7.779 | BV | 0.0328 | 1.32053e4 | 6202.66650 | 0.28397 |
| 11 | 7.897 | VP | 0.0341 | 3038.55884 | 1357.19727 | 0.06534 |
| 12 | 9.588 | BV | 0.0337 | 8135.68994 | 4005.47656 | 0.17495 |
| 13 | 15.598 | VV | 0.0411 | 5282.31689 | 2117.66187 | 0.11359 |
| 14 | 15.757 | VP | 0.0448 | 1.58142e4 | 5625.49463 | 0.34007 |
| 15 | 16.031 | VB | 0.0425 | 2916.84033 | 1114.82434 | 0.06272 |
| 16 | 16.916 | BB | 0.0478 | 2663.63843 | 867.89441 | 0.05728 |
| 17 | 18.660 | VV | 0.0961 | 1.24115e6 | 1.72195e5 | 26.69016 |
| 18 | 18.834 | VV | 0.0511 | 2.57049e5 | 7.67654e4 | 5.52766 |
| 19 | 27.425 | VV | 0.3116 | 2674.28418 | 103.44904 | 0.05751 |
| 20 | 28.355 | BV | 0.0607 | 2.16132e5 | 5.40068e4 | 4.64778 |
| 21 | 28.492 | VV | 0.0551 | 5.41157e4 | 1.53480e4 | 1.16372 |
| Totals: | | | | 4.65023e6 | 1.03654e6 | |

Synthesis of 5-Decenyl Acetate:
Major Component of the Peach Twig Borer Pheromone Synthesis of 5-Decenyl Acetate:
Major Component of the Peach Twig Borer Pheromone Synthesis of 9-Tetradecenyl Formate:
Pheromone Analog of the Diamondback Moth (DBM)

Synthesis of 11-Tetradecenyl Acetate:
Pheromone of the Omnivorous Leafroller(OLR)

Synthesis of E-4-Tridecenyl Acetate:
Major Component of the Tomato Pinworm (TPW) Pheromone Synthesis of E.E.-8, 10-Dodecadienol
Codling Moth (CM) Pheromone

US 6,215,019 B1

SYNTHESIS OF 5-DECENYL ACETATE AND OTHER PHEROMONE COMPONENTS

This application derives priority from U.S. Provisional Application No. 60/098,792, filed Sep. 1, 1998.

TECHNICAL FIELD

The present invention relates to synthetic pheromones and, in particular, to an improved synthesis of E-5-decenyl acetate, the major component of the Peach Twig Borer pheromone (PTB pheromone).

BACKGROUND OF THE INVENTION

The Peach Twig Borer (PTB) is a major pest in stone fruit orchards. One pest control method currently employed involves spraying orchards with insecticides. This method is problematic in various ways. Insecticides are applied directly to the fruit, a practice that is contrary to an increasing preference for organic produce as well as contrary to water quality issues and other environmental concerns. Insecticides are also nondiscriminate killers and kill beneficial insects as well as harmful insects. Finally, the PTB is becoming resistant to many of the common insecticides.

An alternative method to control insect populations involves the use of the insect's sex attractant to confuse the male insect and thereby prevent mating and eliminate future insect generations. This technique is called mating pattern disruption. The biggest problem in using mating pattern disruption to control insect populations is the cost of producing the insect pheromone. Usually the cost of insect pheromone application is the same as or greater than traditional insecticide applications. Methods that reduce the production costs of insect pheromones would make mating pattern disruption an economical technique for controlling insect populations.

PTB pheromone is an 85:15 ratio of E-5-decenyl acetate and E-5-decenol. Thus production of 5-decenyl acetate, which is the major component of PTB pheromone, is a significant step of the PTB pheromone manufacturing process. The acetate can be subsequently removed by hydrolysis to obtain E-5-decenol, the other component of PTB pheromone.

A fast, inexpensive, and high yield process for synthesizing E-5-decenyl acetate is, therefore, desirable.

SUMMARY OF THE INVENTION

An object of the invention is, therefore, to improve the process for manufacturing PTB pheromone.

FIGS. 1A, 1B, 1C, and 1D (collectively FIG. 1) depict a recent method of producing 5-decenyl acetate disclosed in U.S. Pat. No. 5,916,983 of Pederson and Grubbs. The synthesis produces 1-chlorohexene by coupling allyl magnesium chloride and bromochloropropane. A 40 percent yield of a 60:40 isomeric ratio of trans:cis 1-chloro-5-decene is then obtained by olefin metathesis of 1-chlorohexene and 1-hexene. The metathesis catalyst used in this process is bis(tricyclohexylphosphine)dichloro ruthenium (II) benzylidene $[(PCy_3)_2Cl_2]Ru=CBPh$, referred to as "Grubbs' catalyst." These reactions were performed between 32° C. and 62° C., because at room temperature, the reaction is slow and conversions are lower. A 27 percent yield was obtained when the reaction was run at 32°. 1-Chloro-5-decene is converted to 5-decenyl acetate by heating the former with potassium acetate in acetic acid. The resulting 60:40 ratio of trans:cis 5-decenyl acetate is isomerized to an 80:20 ratio of trans:cis 5-decenyl acetate by the sodium salt of benzenesulfinic acid in acetic acid.

The low 25 to 27 percent gross yield of 5-decenyl acetate is largely due to the formation of a methylidene ruthenium catalyst intermediate, which is a thermodynamically stable alkylidene that prevents high conversion of starting materials to products and prevents the formation of a high trans isomeric product.

This method typically required 18 to 25 days to produce 12 Kg of 5-decenyl acetate in an 80:20 cis:trans ratio using standard-sized equipment (multiple reactions needed to be run because of low yields and many of the reactions needed to be diluted with solvents to work properly). In particular, five days were required to run the reaction and to work up and distill the 1-chloro-5-decene. Three metathesis runs at one day each, plus two days to remove the catalyst, and 2 days to distill, were needed to produce the 1-chloro-5-decene for a subtotal of seven days. The subsequent production of 5-decenyl acetate with a trans:cis ratio of 60:40 required two to three runs at 36 to 48 hours each to achieve 98 percent conversion, for a subtotal of four to six days. Twenty-four hours for each of two batches were required to achieve the isomerization of 5-decenyl acetate to an 80:20 ratio of trans:cis, for a subtotal of two days. The total time of 18 to 25 days does not include the time for the final distillation.

Although the 20 percent cis-5-decenyl acetate does not affect the efficacy of the PTB pheromone in lures and mating disruption applications, the low yield and the long completion time make the process expensive. In view of the numerous reaction steps, the large amount of required starting materials and reagents, the long reaction times, and/or the overall low yield, this manufacturing process for 5-decenyl acetate is still not satisfactory.

The invention provides, therefore, an improved synthesis of E-5-decenyl acetate that eliminates many of the problems associated with the previous method. The improved synthesis employs fewer reaction steps, uses stable and readily available starting materials, has a shorter reaction time, and provides a good product yield without the need for expensive and sophisticated equipment. In a preferred embodiment, the improvements include: 1) a technique to obtain higher conversion of starting materials to products (from 40 percent to greater than 75 percent); 2) an increase in the metathesis trans:cis ratio from 60:40 to between 80:20 to 84:16; 3) only two reaction steps; and 4) a production time of less than a week.

In the preferred embodiment, certain of these improvements are accomplished by self-metathesizing 1-hexene to 5-decene followed by cross-metathesizing of 5-decene and 5-hexenyl acetate. The self-metathesis of 1-hexene is performed in the presence of Grubbs' catalyst $[(PCy_3)_2Cl_2]$ Ru=CHPh. Further, the ethylene side product is allowed to bubble out of solution. The 5-decene produced by the self-metathesis is cross-metathesized with 5-hexenyl acetate to yield greater than 98 percent pure 5-decenyl acetate with an 80:20 to 84:16 trans:cis ratio. The reaction is performed in the presence of Grubbs' catalyst and under vacuum in order that the side product 1-hexene is removed from solution. The elimination of 1-hexene prevents the formation of the methylidene catalyst intermediate and leads to an increased yield and a more desirable trans isomeric product ratio (86:14 as compared to the earlier 60:40).

In a more general embodiment, the invention provides a method for synthesizing olefinic alcohols, acetates, aldehydes, carboxylic acids or derivatives thereof by self-metathesizing a first alpha olefin in an exemplary form of $CH_2CH(CH_2)_n(CHX)(CH_2)_mCH_3$, where X is selected from a hydrogen, alcohol, acetate, halide, tosylate, or mesylate or derivative thereof, and n and m are each selected from zero and an integer less than or equal to 20, in the presence of a first catalyst to form a product in the form of $CH_2CH(CH_2)_p(CHX)(CH_2)_qCH_3$, where p and q are each selected from zero and an integer such that at least p is greater than n or at least q is greater than m and a first side product in the form of $CH_2Y$, where Y is selected from $CH_2$ or $CH(CH_2)_n(CHX)(CH_2)_mCH_3$; and then cross-metathesizing the product with a second alpha olefin in an exemplary form of $NCH(CH_2)_rM$, where N is selected from $CH_2$ or $CH(CH_2)_rM$, r is selected from zero and an integer less than or equal to 20, and M is selected from an alcohol, acetate, aldehyde, halide, carboxylic acid, or derivative thereof in the presence of a second catalyst to form $CH_3(CH_2)_m(CHX)(CH_2)_nCHCH(CH_2)_rM$ or derivatives thereof and a second side product in the form of $CH_2Z$, where Z is selected from $CH_2$ or $CH(CH_2)_n(CHX)(CH_2)_mCH_3$ under conditions of sufficiently high temperature and/or sufficiently low pressure (vacuum) such that the second side product evaporates out of the reaction mixture.

Additional objects and advantages of this invention will be apparent from the 5 following detailed description of preferred embodiments thereof, which proceeds with reference to the accompanying drawings.

DETAILED DESCRIPTION OF PREFERRED EMBODIMENTS

Figures 1A, 1B, 1C, 1D:
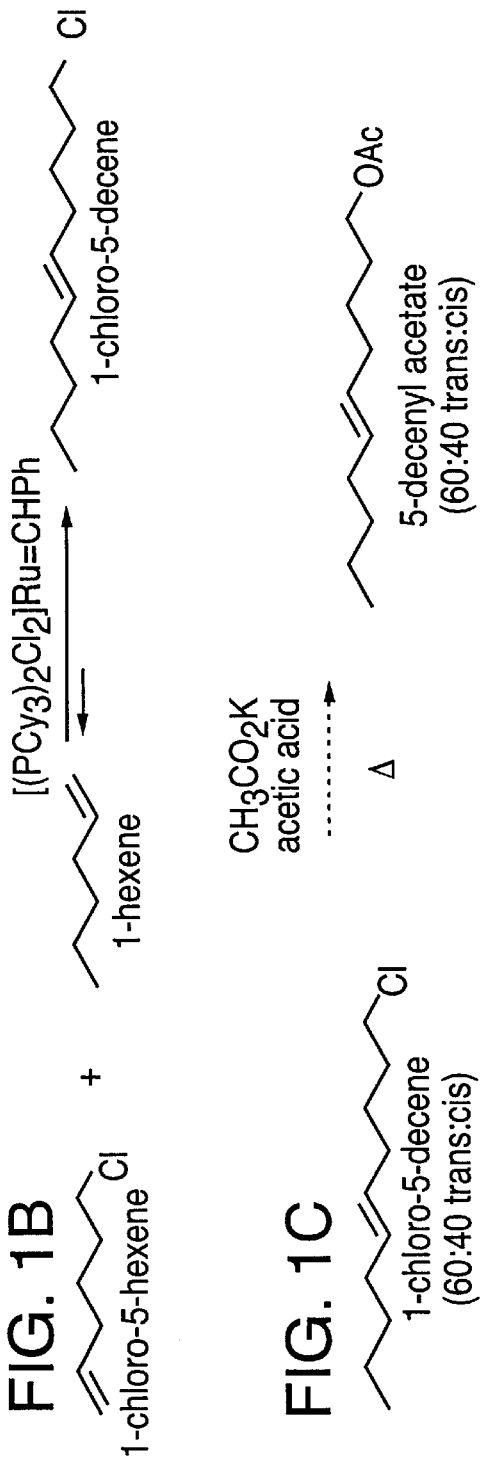
FIG. 1A is a reaction diagram showing a portion of a synthesis (olefin metathesis) of 5-decenyl acetate, in which allyl magnesium chloride is reacted with bromochloropropane to yield 1-chloro-5-hexene, as disclosed in U.S. Pat. No. 5,916,983.
FIG. 1B is a reaction diagram showing the second step of the synthesis of 5-decenyl acetate, in which 1-chloro-hexene is reacted with 1-hexene in the presence of Grubbs' catalyst to yield 1-chloro-5-decene.
FIG. 1C is a reaction diagram showing the third step of the synthesis of 5-decenyl acetate, in which 1-chloro—5—decene is heated with potassium acetate to yield 5-decenyl acetate.
FIG. 1D is a reaction diagram showing the fourth step of the synthesis of 5-decenyl acetate, in which a 60:40 trans:cis ratio of 5-decenyl acetate is isomerized in the presence of the sodium salt of benzenesulfinic acid and acetic acid to yield an 80:20 trans:cis ratio of 5-decenyl acetate.

In general, the invention provides a method for synthesizing olefinic alcohols, acetates, aldehydes, carboxylic acids or derivatives thereof in a reaction chamber by self-metathesizing a first alpha olefin in an exemplary form of $CH_2CH(CH_2)_n(CHX)(CH_2)_mCH_3$, where X is selected from a hydrogen (H), an alcohol (OH), an acetate (AcO), a halide (Cl, Br, I), a tosylate (TsO), or a mesylate (MesO) or derivative thereof, and n and m are each selected from zero and an integer less than or equal to 20, in the presence of a first catalyst to form a product in the form of $CH_2CH(CH_2)_p(CHX)(CH_2)_qCH_3$, where p and q are each selected from zero and an integer such that at least p is greater than n or at least q is greater than m and a first side product in the form of $CH_2Y$, where Y is selected from $CH_2$ or $CH(CH_2)_n(CHX)(CH_2)_mCH_3$; and then cross-metathesizing the product with a second alpha olefin in an exemplary form of $NCH(CH_2)_rW$, where N is selected from $CH_2$ or $CH(CH_2)_rM$, r is selected from zero and an integer less than or equal to 20, and M is selected from an alcohol, acetate, aldehyde, halide, or carboxylic acid or derivative thereof in the presence of a second catalyst to form $CH_3(CH)_m(CHX)(CH)_nCHCH(CH_2)_rM$ or derivatives thereof and a second side product in the form of $CH_2Z$, where Z is selected from $CH_2$ or $CH(CH_2)_n(CHX)(CH_2)_mCH_3$ under conditions of sufficiently high temperature and/or sufficiently low pressure such that the second side product evaporates out of the reaction chamber. The step of self metathesizing may also preferably be performed under conditions of sufficiently high temperature and/or sufficiently low pressure such that the first side product evaporates out of the reaction chamber.

The first and second catalysts are metathesis catalysts described in detail below, and each given synthesis preferably employs the same catalyst for the self-metathesis and cross-metathesis reactions.

Metathesis catalysts of the structure $[(PL_3)_2AA']$Ru=CRR' are generally preferred, wherein:

L is selected from $-CR_4(R_5)_2$ and cycloalkyl or alkyl-substituted cycloalkyl wherein the number of carbon atoms in the ring is from 4 to 12;

$R_4$ and $R_5$ are each selected from hydrogen and alkyl;

A and A' are anionic ligands independently selected from halogen, hydrogen, $C_1$–$C_{20}$ alkyl, aryl, $C_1$–$C_{20}$ alkoxide, aryloxide, $C_2$–$C_{20}$ alkoxycarbonyl, arylcarboxylate, $C_1$–$C_{20}$ carboxylate, arylsulfonyl, $C_1$–$C_{20}$ alkylsulfonyl, $C_1$–$C_{20}$ alkylsulfinyl, each ligand optionally being substituted with $C_1$–$C_5$ alkyl, halogen, $C_1$–$C_5$ alkoxy or with a phenyl group that is optionally substituted with halogen, $C_1$–$C_5$ alkyl or $C_1$–$C_5$ alkoxy; and R and R' are independently selected from hydrogen, $C_1$–$C_{20}$ alkyl, aryl, $C_1$–$C_{20}$ carboxylate, $C_1$–$C_{20}$ alkoxy, aryloxy, $C_1$–$C_{20}$ alkoxycarbonyl, $C_1$–$C_{20}$ alkylthio, $C_1$–$C_{20}$ alkylsulfonyl and $C_1$–$C_{20}$ alkylsulfinyl, each of R and R' optionally substituted with $C_1$–$C_5$ alkyl, halogen, $C_1$–$C_5$ alkoxy or with a phenyl group that is optionally substituted with halogen, $C_1$–$C_5$ alkyl or $C_1$–$C_5$ alkoxy. These catalysts are generically described by Grubbs et al. in International Application No. PCT/US95/09655.

One catalyst of this type, $[(PCy_3)_2Cl_2]Ru$=CHPh, Grubbs' catalyst is particularly preferred, and an example of its synthesis is described below.

Synthesis of Grubbs' Catalyst

A solution of $RuCl_2$ $(PPh_3)_3$ (4.0 g 4.17 mmol) in $CH_2Cl_2$ (40 mL) was treated at $-78°$ C. with a $-50°$ C. solution of phenyldiazomethane (986 mg 8.35 mmol, 2.0 eq) in pentane (10 mL). Upon addition of the diazo compound, an instantaneous color change from orange-brown to green-brown and vigorous bubbling was observed. After the reaction mixture was stirred at $-70$ to $-60°$ C. for 10 minutes an ice-cold solution of tricyclohexylphosphine $(PCy_3)$ (2.57 g 9.18 mmol, 2.2 eq) in $CH_2Cl_2$ was added by syringe. The solution was allowed to warm to room temperature for 30 minutes while stirring, and exhibited a color change from brown-green to red. The solution was filtered, concentrated to half its original volume and filtered a second time. Methanol (100 mL) was added to precipitate a purple microcrystalline solid, which was filtered, washed several times with acetone and methanol (10 mL portions) and dried under vacuum for several hours to yield 3.40 g $[(PCy_3)_2Cl_2]$Ru=CHPh (99%).

Grubbs' catalyst is commercially available at a purity of greater than 95 percent from Boulder Scientific of Boulder, Colo.

Figure 2:
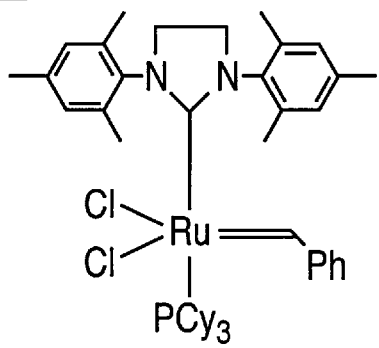
FIG. 2 is a structural diagram of an embodiment of an alternative metathesis catalyst, Catalyst 2.

In addition, a new catalyst, catalyst 2, and its family of 1,3-dimesityl-4,5-dihydro-imidazol-2-ylidene-substituted ruthenium-based complexes are also contemplated to metathesize the reactions disclosed herein. The chemical structure of catalyst 2 is shown in FIG. 2. The synthesis of catalyst 2 is described in Organic Letters, "Synthesis and Activity of a New Generation of Ruthenium-Based Olefin Metathesis Catalysts Coordinated with 1,3-Dimesityl-4,5-dihydro-imidazol-2-ylidene Ligands," Scholl et al. (1999).

Other metathesis catalysts such as "well defined catalysts" could be alternatively be employed. Such catalysts include, but are not limited to, Schrock's molybdenum metathesis catalyst, 2,6-diisopropylphenylimido neophylidenemolybdenum (VI) bis(hexafluoro-t-butoxide), described by Grubbs et al. in *Tetrahedron* (1998), 54, 4413–4450 and Basset's tungsten metathesis catalyst described in Couturier, J. L. et al. *Angers. Chem. Int. Ed. Engl.* (1992) 31,628. Schrock's catalyst is available from Strem (Newburyport, Mass.), but is too expensive for large scale production of PIB pheromone. Basset's catalyst is not presently commercially available, is sensitive to air, water, and a variety of functional groups, and is expensive to synthesize.

Other metathesis catalysts such as "non-well defined catalysts" could also be employed, but their activity depends on co-catalysts, which are typically heavy metals such as tetraalkyl tin or tetraalkyl lead compounds and present a waste disposal issue. These non-well defined catalysts also require for activation the presence of strong Lewis acids, which may cause undesirable double bond migration.

The following reactions, figures, and examples are shown herein only by way of example to the above-described type of metathesis syntheses and should not be considered as limiting the scope of the invention.

Figure 3A:
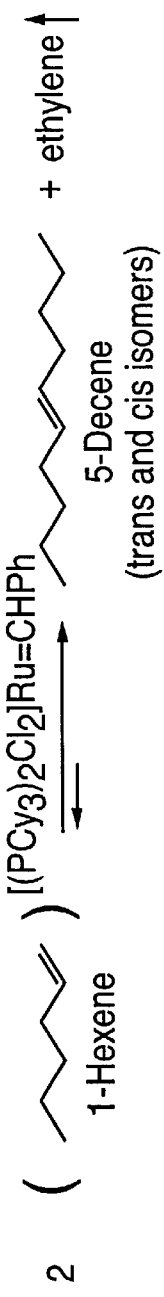
FIG. 3A shows a first step of an improved synthesis of 5-decenyl acetate, in which 1-hexene is self-metathesized to 5-decene in the presence of Grubbs' catalyst and ethylene is removed from the reaction by venting to atmosphere.
Figure 3B:
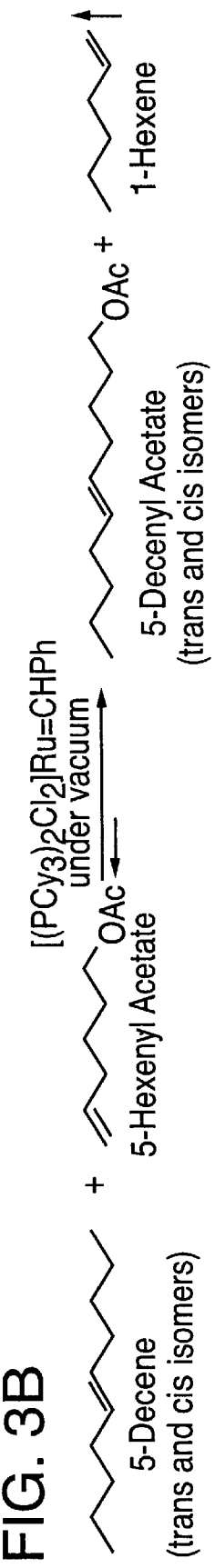
FIG. 3B shows a second step of an improved synthesis of 5-decenyl acetate, in which 5-decene is reacted with 5-hexenyl acetate in the presence of Grubbs' catalyst and under vacuum to yield 1-hexene and an 80:20 to 84:16 trans:cis ratio of 5-decenyl acetate.

FIG. 3 shows an improved synthesis of 5-decenyl acetate. In particular, FIG. 3A shows the self-metathesization of 1-hexene to form 5-decene in the presence of Grubbs' catalyst. The reaction favors 5-decene formation because ethylene is removed from the reaction as it is formed. FIG. 3B shows the cross-metathesization of 5-decene and 5-hexenyl acetate (5-hexen-1-yl acetate) in the presence of Grubbs' catalyst and under vacuum. Running the reaction under vacuum removes 1-hexene and results in high conversions of 5-hexenyl acetate to 5-decenyl acetate and an 84:16 trans: cis ratio of isomeric products. The following examples demonstrate the preparation of the PTB pheromone, but should not be regarded as a limitations to the scope of the invention.

EXAMPLE 1

Synthesis of 5-Decene: Self-Metathesis of 1-Hexene

With reference to FIG. 3A, to a dry 2-L round-bottomed flask was added 225 g (2.67 mol) 1-hexene (available from Amoco at a purity of greater than 95%) and a magnetic stir bar. The flask was sparged with nitrogen for 10 minutes. Grubbs' catalyst $[(PCy_3)_2Cl_2]$Ru=CHPh (2.2 g, 2.7 mmol) was added and the reaction was stirred at room temperature for 18 hours. The evolution of ethylene gas from the reaction was observed. The spent catalyst was removed by filtering the reaction through 200 g of J. T. Baker Silica Gel 60–200 mesh in a 1.5 inch×22 inch chromatography column. The column was rinsed with 300 mL of petroleum ethers (38° C. to 55° C. boiling point). The solvent and unreacted 1-hexene were removed under reduced pressure to yield 115 g (0.81 mol) of 5-decene. This product was used in the next reaction without further purification.

Synthesis of 5-Decenyl Acetate: Cross Metathesis of 5-Decene and 5-Hexenyl Acetate With reference to FIG. 3B, to a dry 1-L round-bottomed flask was added 115 g (0.81 mol) 5-decene, 22.5 g (0.158 mol) 5-hexenyl acetate (available from TCI America under the name of acetic acid 5-hexenyl ester at a purity of greater than 98%), and a magnetic stirbar. The flask was sparged with nitrogen for 5 minutes, Grubbs' catalyst 1.33 g (1.6 mmol) was added, and the flask was run under an 8 mmHg vacuum for 16 hours. After 16 hours, the vacuum pump was removed and the reaction was stirred for an additional 12 hours under a nitrogen atmosphere. GC analysis indicated 87 percent 5-decenyl acetate, 12 percent 1,10-diacetoxy-5-decene, and less than one percent 5-hexenyl acetate.

A purified sample of 5-decenyl acetate was obtained by filtering about half of the reaction mixture through 500 g of J. T. Baker silica gel in a 1.5 inch×22 inch chromatography column. The column was rinsed with 1 L of petroleum ether, followed by rinsing with 1 L of 10 percent diethyl ether in petroleum ether. Two hundred-milliliter fractions were collected. The data are summarized below.

| | GC Results | | |
|---|---|---|---|
| Fraction Number | 5-decene | 5-decenyl acetate | 1, 10-diacetoxy-5-decene |
| 1 | 0 | 0 | 0 |
| 2 | 100 | 0 | 0 |
| 3 | 91 | 9 | 0 |
| 4 | 0 | 100 | 0 |
| 5 | 0 | 100 | 0 |
| 6 | 0 | 100 | 0 |
| 7 | 0 | 100 | 0 |
| 8 | 0 | 0 | 0 |
| 9 | 0 | 0 | 100 |
| 10 | 0 | 0 | 100 |
| 11 | 0 | 0 | 0 |

Fractions 4, 5, 6, and 7 were combined and concentrated under reduced pressure to yield 10.6 g (53.5 mmol) of 99.4 percent chemical purity and a 81:19 trans:cis isomeric ratio. This sample of 5-decenyl acetate was substantially indistinguishable from a sample of 5-decenyl acetate obtained from Consep, Inc. of Bend, Oreg. E-5-decenyl acetate and Z-5 decenyl acetate are commercially available from Sigma (St. Louis, Mo.) at $54.60 per 500 mg ($109.20/g) and $55.00 per 500 mg ($110.00/g), respectively.

EXAMPLE 2

Synthesis of 5-Decene: Self-Metathesis of 1-Hexene

With reference again to FIG. 3A, to a clean 72 L round bottomed flask connected to a pneumatic overhead stirrer (a high efficiency reflux condenser with −10° C. circulating coolant) was added 48L (384 mol) of 1-hexene (obtained from Amoco at a purity of greater than 99 percent and used without further purification). Stirring was initiated and the solution was sparged with nitrogen from below the surface for 15 minutes. Grubbs' catalyst (10 g, 0.018 mol) was added and stirred under a nitrogen atmosphere for 18 to 24 hours. The ethylene was vented through the high efficiency condenser into an exhaust duct.

After 24 hours, GC analysis indicated 60 to 70 percent conversion of 1-hexene to 5-decene. This reaction mixture was filtered through 2.5 Kg of silica gel (Fisher 170–400 mesh, 60 Å) to remove the spent catalyst.

Skilled persons will appreciate that the materials can be carried through the these reactions without purification of the intermediate compounds. However, if purification is desired, the intermediates can be isolated, e.g. the 5-decene can be distilled or otherwise purified.

Synthesis of 5-Decenyl Acetate: Cross Metathesis of 5-Decene and 5-Hexenyl Acetate With reference again to FIG. 3B, a clean 72 L round bottomed flask was loaded with 60 L of 5-decene (60% to 70% purity) and connected to a pneumatic overhead stirrer and a vacuum distillation setup. The vacuum distillation set up included a 3"×36" distillation column and a high efficiency heat exchanger and 1" take-off head which ran to a 22 L receiving flask. Two vacuum traps were inserted after the 22 L receiving flask and in front of the high capacity vacuum pump.

Grubbs' catalyst (100 g, 0.122 mol) was added to the round bottom flask, stirring was initiated, a vacuum was applied, and the heating mantels were turned to setting 2. The temperature of the reaction mixture was maintained below 45° C., and the vacuum pressure was adjusted to prevent 5-decene from distilling out of the 72 L flask. 5-Hexenyl acetate (99% purity, 12L, 76 mol) was added over 5 hours. After the addition was completed, the heating mantels were turned off, and the reaction was stirred under a 10 mmHg vacuum. After 12 hours, the vacuum traps were emptied and repacked with dry ice, and vacuum was applied again.

Skilled persons will appreciate that the metathesis reactions are preferably conducted between about 25° C. and 60° C., depending on the vacuum being pulled on the reaction, and most preferably between about 25° C. and 35° C. at about 10 mmHg.

GC analysis of the metathesis reaction indicates 0.1% 1-hexene, 64.9% 5-decene, 0.08% 5-hexenyl acetate, 30.8% 5-decenyl acetate (82% trans and 18% cis isomers), and 4.1% 1,10-diacetoxy-5-decene.

Figure 4A:
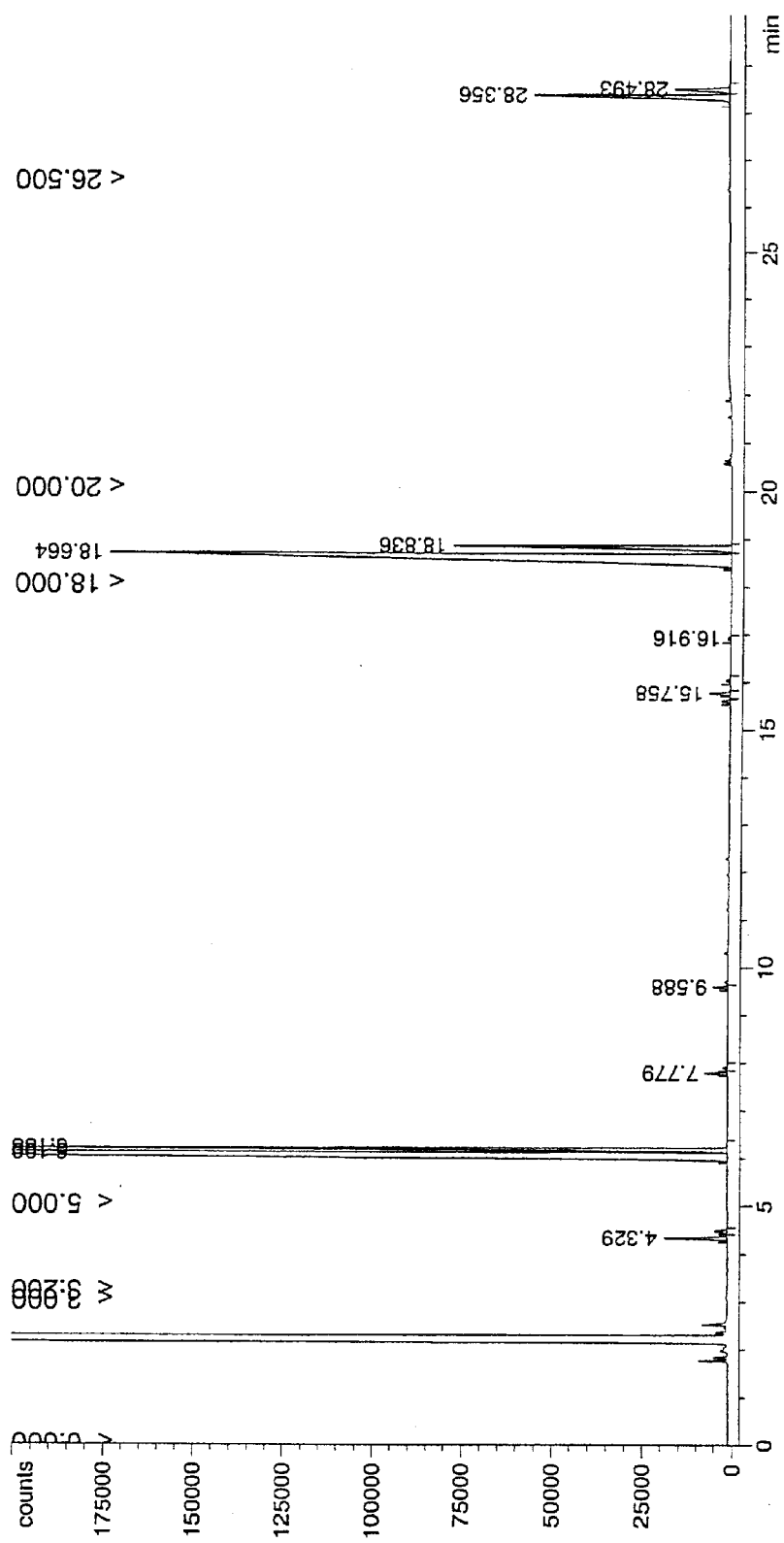
FIG. 4 is a representative GC chromatogram of a completed 5-decenyl acetate metathesis reaction mixture prepared in accordance with the present invention.

FIG. 4 is a representative GC chromatogram of a completed 5-decenyl acetate metathesis reaction mixture. The GC column was a J&W Scientific DB-225 capillary with a 30 m×0.25 mm×0.25 μm film thickness. The GC method was characterized by an initial temperature of 40° C., an initial time of one minute, a first rate of 8° C./minute, a temperature of 140° C., a second rate of 20° C./minute, a final temperature of 210° C., and a final time of 8 minutes. The samples were run on a HP 5890 GC with FID detection running 100:1 split and a head pressure of 17 psi. With w reference to FIG. 3, the relevant peaks are identified below:

| Peak Sample | Name |
|---|---|
| Rt 1.833 min | 1-hexene |
| Rt 6.095 min | E-5-decene |
| Rt 6.186 | Z-5-decene |
| Rt 10.210 min | 5-hexenyl acetate (not detected in this chromatogram) |
| Rt 18.660 min | E-5-decenyl acetate |
| Rt 18.834 min | Z-t-decenyl acetate |
| Rt 28.355 min | 1,10-diacetoxy-E-5-decene |
| Rt. 28.492 min | 1,10-diacetoxy-Z-5-decene |

The large peak between Rt 2.000 and 2.300 min is cyclohexane which is used to dilute the GC samples, it was not integrated.

Yields ranging from 54 to 83 percent have been obtained at the 12 Kg scale. The yield can be manipulated by changing the ratio of 5-decene to hexenyl acetate. Because the 1-hexene is removed under the strong vacuum, increasing the ratio of 5-decene increases the yield of 5-decenyl acetate; however, this increased ratio decreases the throughput, i.e. decreases the number of Kg of 5-decenyl acetate made in a run. At the 12 Kg scale, a 75:25 ratio of 5-decene:1-hexene to a 50:50 of 5-decene:1-hexene will work to convert greater than 99 percent of 5-hexenyl acetate into 5-decenyl acetate and 1,10-diacetoxy-5-decene.

The high conversion of starting materials to products resulting from running the reaction under vacuum was unexpected. The application of vacuum was attempted to remove ethylene in the hope of enhancing the conversion up to about 75 percent; however, the removal of 1-hexene to obtain greater than a 99 percent conversion of 5-hexenyl acetate was completely unexpected.

The preferred embodiments reduce the number of synthetic steps from four to two and reduce the amount of time required to synthesize the end product from over 20 days to as few as two days with the same scale of materials and same type of equipment. This represents a time reduction by a factor of ten. By employing the procedure of Example 2, a skilled person can produce 12 Kg of 5-decenyl acetate in an 83:17 trans:cis ratio in 48 hours or less. This process time includes the metathesis reactions and catalyst removal, but does not include the final distillation.

In addition to being more expedient, the present process also reduces the cost of production of 5-decenyl acetate. For example, present process has been demonstrated to produce 5-decenyl acetate in the preferred trans:cis ratio for a cost of generally less than $0.40 per gram. The lack of waste solvents and waste products substantially reduces the cost of the reactions, including the costs of both purchasing the solvents and disposing of the waste. A further advantage is that the starting materials, such as 1-hexene and 5-hexenyl acetate, are commercially available.

Catalyst Removal Procedure

The metathesis catalyst is removed by a water soluble phosphine (i.e. trishydroxymethyl phosphine (THMP)). THMP is made from tetrakis hydroxymethyl phosphonium chloride (TKC) as described by J. W. Ellis et al. *Inorg. Chem.* (1992) 31,3026 and N. J. Goodwin et al. *Chem. Commun.* (1996) 1551. TKC is in an 80 percent solution in water.

The metathesis reaction mixture from Example 2 above (20 L containing approximately 0.041 mol of metathesis catalyst) was added to a 22 L flask that was connected to a pneumatic overhead stirrer and placed in a 55° C. sand bath. The THP solution was added and reaction was vigorously stirred for 12 to 24 hours. Nitrogen sparged water (2L) was added and vigorously stirred for one hour. Stirring was stopped and the phases separated. The bright orange aqueous phase was removed, and another 2 L of water was added and stirred vigorously for 30 minutes. Again the phases were separated and the aqueous phase was removed. This procedure was repeated until the aqueous phase was colorless, which is usually 3 to 4 washing. The organic phase was washed with 1 L of 4 M HCl for 30 minutes (pH preferably <1) and removed. Sodium bicarbonate saturated water (1L) was added and stirred vigorously for 15 minutes (pH preferably >7). The aqueous phase was separated and removed.

To the vigorously stirring 5-decenyl acetate solution was added 400 g of anhydrous sodium sulfate. After two hours of stirring, 400 g of potassium carbonate was added and the flask was stirred for 10 to 12 hours at 55° C.

After 12 hours, the stirring was stopped and the 5-decenyl acetate mixture was transferred to a phenolic lined 55 gallon drum and stabilized with 1 M KOH in IPA to make a 0.1% solution. When the drum was full, it was shipped to a vacuum distillation company for purification.

This catalyst removal procedure or silica gel column chromatography can be used to remove the metathesis catalyst from the 5-decene or 5-decenyl acetate reaction mixtures in either the small or large scale processes, as desirable.

Conversion to 5-decenol

A portion of the 5-decenyl acetate can be removed and converted to the corresponding alcohol according to the following procedure and the scale can be adjusted as necessary. 15.0 g (67 mmol) of the 5-decenyl acetate, 35 mL of methanol and 34 mL of 2 M sodium hydroxide is added to a 250 mL round-bottomed flask. This mixture is stirred for 3 hours at room temperature. After 3 hours the hydrolysis is complete, 10 mL of hexane is then added and the solution is washed with 10 mL of 1 M HCl, 10 mL of $NaHCO_3$- saturated water and 10 mL of brine. The organic phase is dried with sodium sulfate and filtered, and the hexane is removed under reduced pressure to yield 9.4 g of 5-decenol. GC analysis shows the isometric ratio of the 5-decenol to be conserved.

Finally, PTB pheromone can be prepared by blending 9.4 g (60.2 mmol) of the 5-decenol and 79.5 g (402 mmol) of the 5-decenyl acetate to make an 87:13 molar mixture of the acetate and alcohol.

EXAMPLE 3

Synthesis of 5-Decenyl Acetate, Employing Catalyst 2

With reference again to FIG. 3A, 5-decene was produced as in Examples 1 or 2 above or with the substitution of catalyst 2 (FIG. 2) for Grubbs' catalyst.

With reference again to FIG. 3B, to a 100 mL round bottomed flask containing a magnetic stirbar and a vacuum adapter was added 10 g (70.4 mmol) 5-hexenyl acetate and 30 g (214 mmol) 5-decene. The reaction was sparged with nitrogen for five minutes, then 20 mg (0.023 mmol) of catalyst 2 (instead of Grubbs' catalyst) was added and stirred under a 10 mm Hg vacuum for eight hours.

The metathesis catalyst was removed as previously described to yield a clear liquid. GC analysis indicated a 78% conversion of 5-hexenyl acetate to 5-decenyl acetate and an 82:18 E:Z isomeric ratio.

EXAMPLE 4

Synthesis of 5-Decenyl Acetate, Employing Catalyst 2

Figure 5:
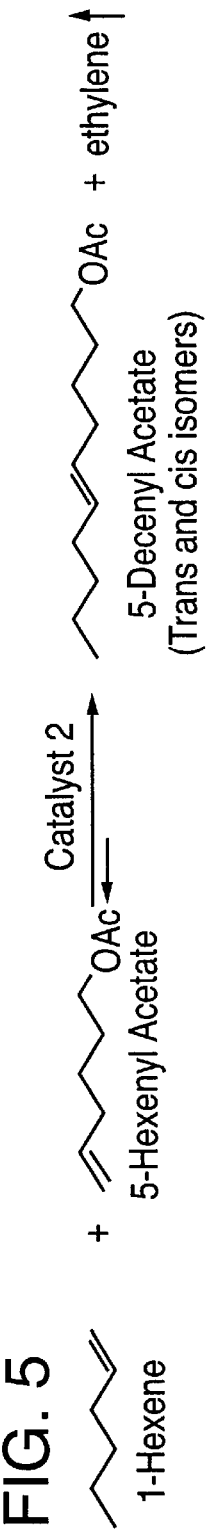
FIG. 5 shows a one step synthesis of 5-decenyl acetate, in which 1-hexene is reacted with 5-hexenyl acetate in the presence of Catalyst 2 to yield an 80:20 to 84:16 trans:cis ratio of 5-decenyl acetate.

FIG. 5 shows a one step synthesis of 5-decenyl acetate in the presence of Catalyst 2 to yield an 80:20 to 84:16 trans:cis ratio of 5-decenyl acetate. With reference to FIG. 3C, to a 100 mL round bottomed flask containing a magnetic stirbar and a reflux condenser was added 10 g (70.4 mmol) 5-hexenyl acetate and 17 g (210 mmol) 1-hexene. The reaction flask was sparged with nitrogen for five minutes, then 24 mg (0.028 mmol) of catalyst 2 (instead of Grubbs' catalyst) was added and stirred under a nitrogen atmosphere at room temperature for six to eight hours. Volatile gasses, including ethylene, were vented into the hood as the reaction proceeded.

The metathesis catalyst was removed as previously described in connection with Grubbs' catalyst, to yield a clear liquid. In an exemplary run, the GC analysis indicated a 65% conversion of 5-hexenyl acetate to 5-decenyl acetate and an 78:22 E:Z isomeric ratio.

This synthesis eliminates the self metathesis reaction of 1-hexene to 5-decene, including the extra starting materials, large quantity of catalyst, and the extra reaction time. In addition, this reaction is feasible without vacuum, can be accomplished in less time than either one of the steps in Examples 1 or 2, and proportionally uses 100 times less catalyst than is used in either of those examples.

Alternative preferred embodiments include: 1) using alcohol protected 5-hexen-1-ol or derivatives thereof, such as but not limited to tetrahydropyranyl (THP) ethers, trimethylsilyl (TMS) ethers, or ethyl vinyl ether (EVE) ethers, or benzoate and propionate esters, or other similar derivatives readily apparent to skilled practitioners); 2) running the cross-metathesis reaction under conditions that prevent the formation of the methylidene ruthenium complex (i.e., removing a volatile terminal olefin as it is formed) since preventing the formation of the methylidene ruthenium complex results in high conversion of starting materials to product; and 3) obtaining a high trans:cis isomeric ratio in the reaction by using the conditions described above.

Figure 6:
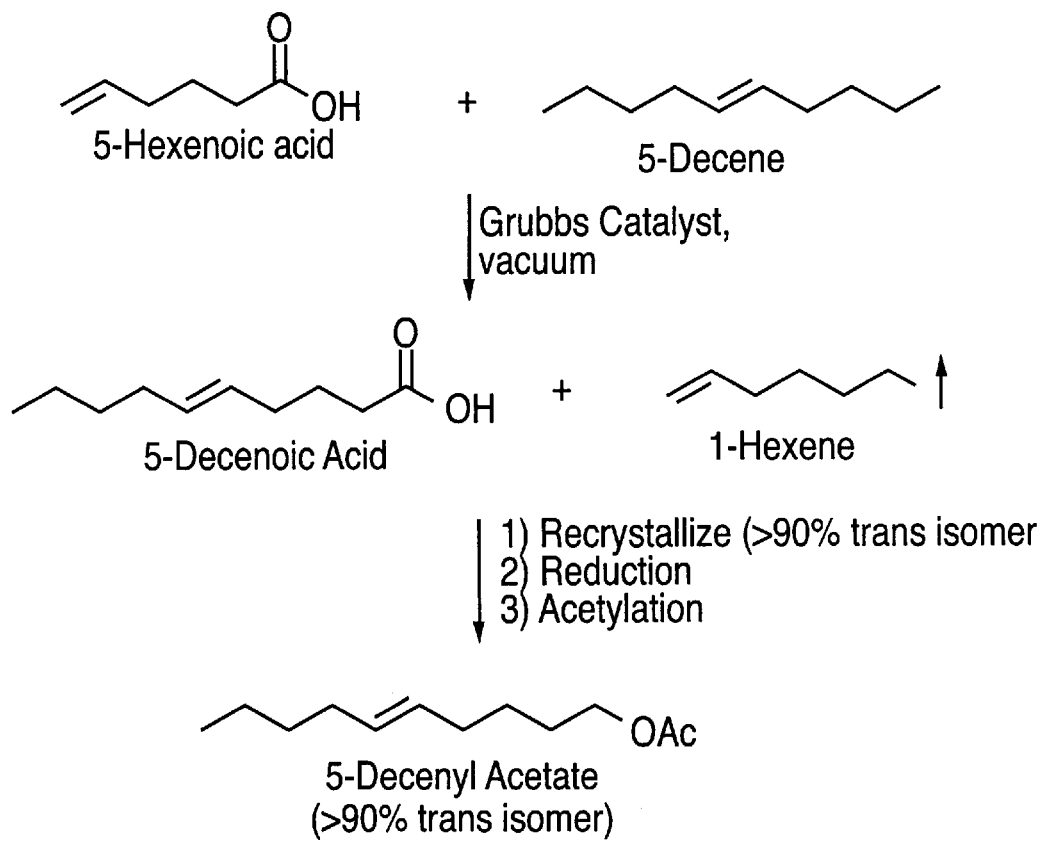
FIG. 6 shows an alternative synthesis of 5-decenyl acetate, in which 1-hexene is reacted with 5-hexenoic acid in the presence of Grubbs' catalyst to produce 5-decenoic acid that can be recrystallized, reduced to an alcohol, and acetylated to yield a greater than 90% E-5-decenyl acetate.
Figure 7:
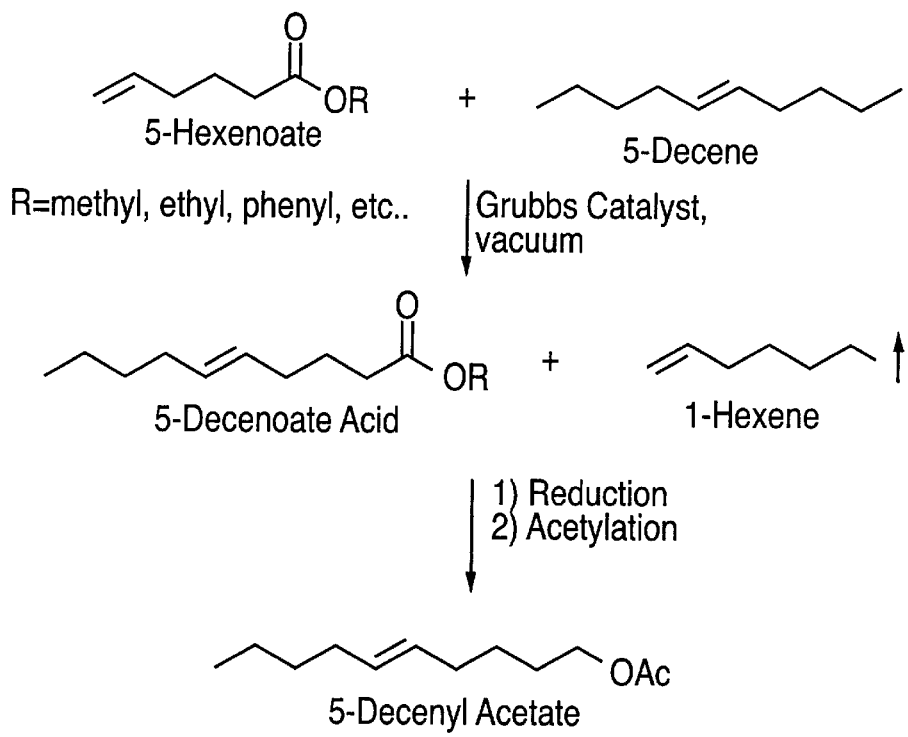
FIG. 7 shows an alternative synthesis of 5-decenyl acetate, in which 1-hexene is reacted with 5-hexenoate ester in the presence of Grubbs' catalyst to produce 5decenoic acid that can be recrystallized, reduced to an alcohol, and acetylated to yield a greater than 90% E-5-decenyl acetate.

For example, 5-hexenoic acid or an ester of 5-hexenoic acid (e.g. methyl 5-hexenoate, ethyl 5-hexenoate, etc.) could be used instead of 1-hexene, but the synthesis would entail a reduction of a carboxylic acid or an ester to an alcohol followed by acetylation. These syntheses are respectively shown in FIGS. 6 and 7. With reference to FIGS. 6 an 7, the 5-hexenoic acid or 5-hexenoate is reacted with 5-decene to form 5-decenoic acid or 5-decenoate, respectively, in the presence of Grubbs' catalyst and under vacuum. The resulting 5-decenoic acid or 5-decenoate are then reacted with 1-hexene, reduced, and acetylated to form 5-decenyl acetate. In addition, synthesizing 5-decenoic acid would have advantages because the salt of 5-decenoic acid could be recrystallized to increase the trans-isomer to greater than 90 percent trans-5-decenoic acid, which is then reduced and acetylated to greater than 90 percent trans-5-decenyl acetate.

Figure 8:
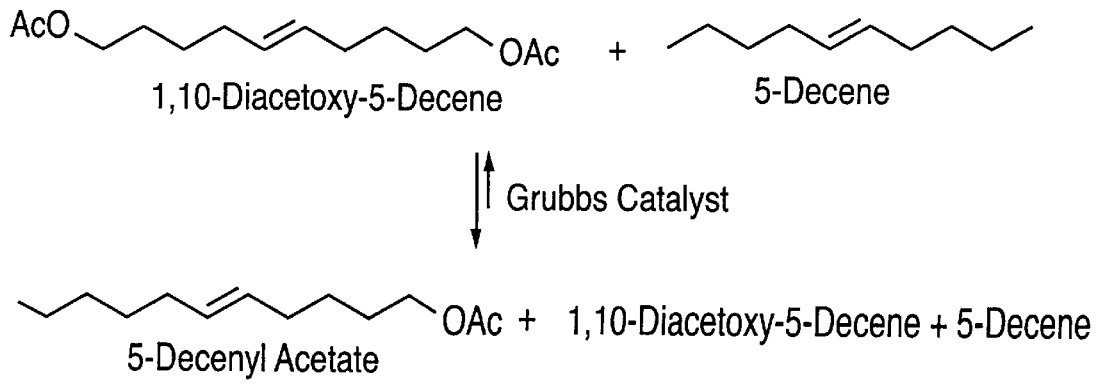
FIG. 8 shows an alternative synthesis of 5-decenyl acetate, in which 5-hexenyl acetate is converted to 1,10-diacetoxy-5-decene, which is then cross-metathesized with 5-decene in the presence of Grubbs' catalyst.

Another way to synthesize 5-decenyl acetate entails the self-metathesis of 5-hexenyl acetate to produce 1,10diacetoxy-5-decene, which is then cross-metathesized with 5-decene. This route is shown in FIG. 8. If no terminal olefins are present (i.e. 1-hexene and 5-hexenyl acetate), the reaction will reach the same conversion and trans:cis ratio as the reactions described in Examples 1 and 2. The conversion of 5-hexenyl acetate to 1,10-diacetoxy-5-decene is preferably run under vacuum to remove ethylene and achieve high conversions (e.g. >98%).

Although the cross metathesis of a 1:1 ratio of 5-decene and 1,10diacetoxy-5-decene statistically yields 25% 5-decene, 50% 5-decenyl acetate, and 25% 1,10-diacetoxy-5-decene, an advantage of this route is to obtain a maximum throughput of starting materials to product. The 5-decene and 1,10-diacetoxy-5-decene would be recycled back into the next cross-metathesis reaction.

Figure 9:
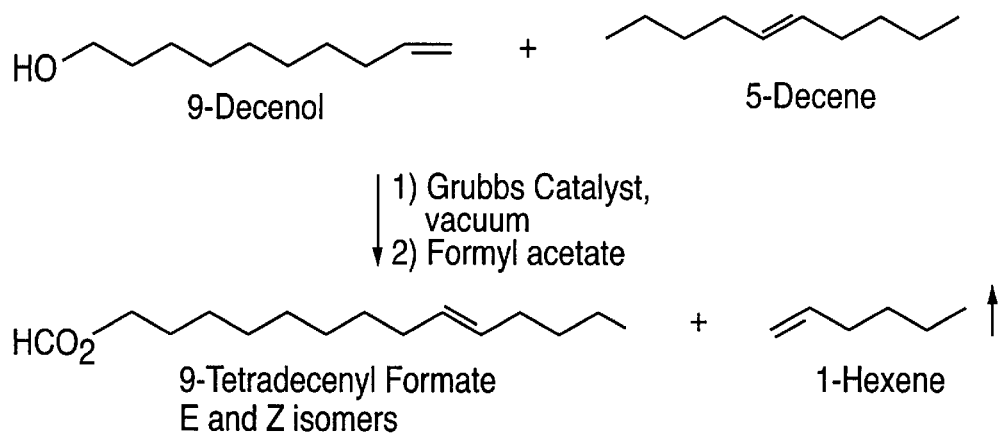
FIG. 9 shows a synthesis of 9-tetradecenyl formate, in which 5-decene is cross-metathesized with 9-decenol in the presence of Grubbs' catalyst to produce 9-tetradecenol while 1-hexene is removed from the reaction under vacuum, and in which the metathesis product, 9-tetradecenol, is reacted with formyl acetate.

FIG. 9 shows a synthesis of 9-tetradecenyl formate, which is an analog of the Diamondback Moth (DBM) pheromone. With reference again to FIG. 3A, 5-decene was produced as in Examples 1 or 2 above or with the substitution of catalyst 2 for Grubbs' catalyst. With reference to FIG. 9, 5-decene is cross-metathesized with 9-decenol under vacuum and in the presence of Grubbs' catalyst to produce 9-tetradecenol (not shown) while 1-hexene is removed from the reaction as it is generated. Then, formyl acetate reacts with the 9-tetradecenol to produce the 9-tetradecenyl formate.

EXAMPLE 6

Synthesis of 11-Tetradecenyl Acetate

Figure 10:
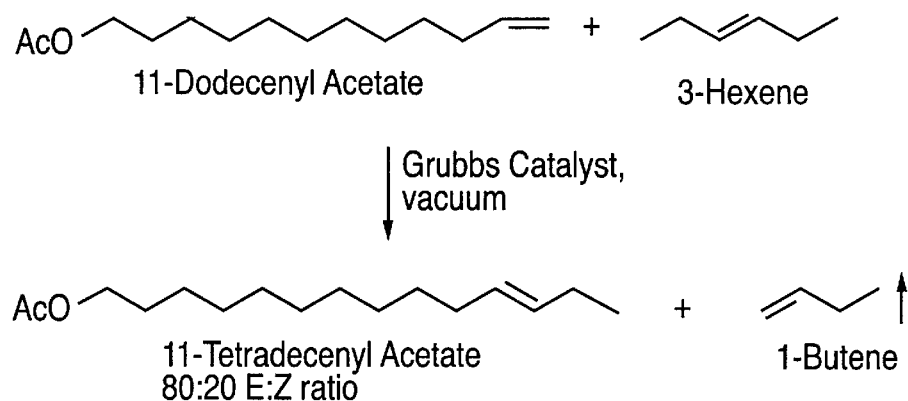
FIG. 10 shows a synthesis of 11-tetradecenyl acetate, in which 3-hexene is cross-metathesized with 11-dodecenyl acetate in the presence of Grubbs' catalyst so that 1-butene is removed from solution as it is generated.

FIG. 10 shows a synthesis of 11-tetradecenyl acetate, which is the pheromone of the Omnivorous leafroller (OLR). With reference to FIG. 10, to a 100 mL round bottomed flask containing a magnetic stirbar and a reflux condenser was added 10 g (44.2 mmol) 11-dodecenyl acetate and 11.2 g (133 mmol) 3-hexene. The reaction was sparged with nitrogen for 5 minutes, then 12 mg (0.014 mmol) of catalyst 2 was added and stirred under a nitrogen atmosphere at room temp for eight hours. Volatile gasses, including 1-butene, were vented into the hood as the reaction proceeded.

The metathesis catalyst was removed, as previously described, to yield a clear liquid. GC analysis indicated a 70% conversion of 11-dodecenyl acetate to 11-tetradecenyl acetate and an 80:20 E:Z isomeric ratio.

EXAMPLE 7

Synthesis of 11-Tetradecenyl Acetate

With reference again to FIG. 10, to a 100 mL round bottomed flask in a −15° C. cooling bath, containing a magnetic stirbar and a dry ice condenser was added 10 g (44.2 mmol) 11-dodecenyl acetate and 15 g (268 mmol) 1-butene. The reaction was sparged with nitrogen for 1 minute, then 24 mg (0.028 mmol) of catalyst 2 was added and stirred under a nitrogen atmosphere at 15° C. for 8 hr., then allowed to warm to room temp overnight. Volatile gasses, including 1-butene, were vented into the hood as the reaction proceeded.

The metathesis catalyst was removed, as previously described, to yield a clear liquid, GC analysis indicated a 55% conversion of 11-dodecenyl acetate to 11-tetradecenyl acetate and an 66:34 E:Z isomeric ratio.

Figure 11:
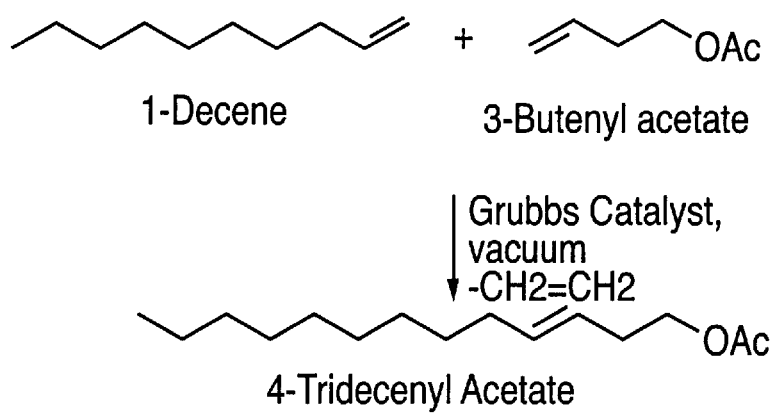
FIG. 11 shows a synthesis of E-4-tridecenyl acetate, in which 1-decene is cross-metathesized with 3-butenyl acetate in the presence of Grubbs' catalyst so that ethylene is removed from solution as it is generated.

FIG. 11 shows a synthesis of E-4-tridecenyl acetate, which is the major component of the Tomato Pinworm (TPW) pheromone. With reference to FIG. 11, 1-decene is cross-metathesized with 3-butenyl acetate in the presence of Grubbs' catalyst under vacuum so that E-4-tridecenyl acetate is produced and ethylene is removed from solution as it is generated.

Figure 12:
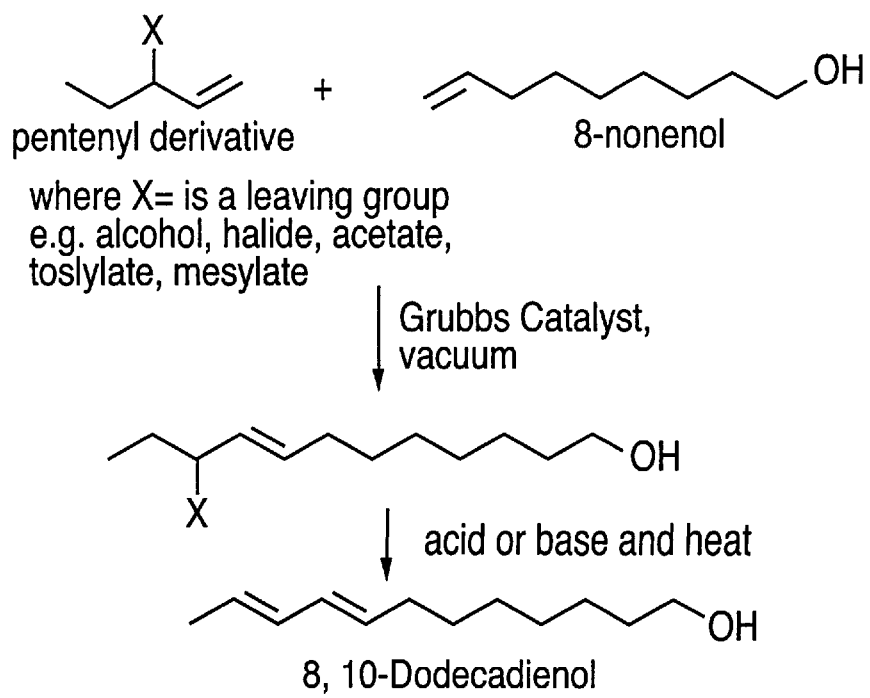
FIG. 12 shows a synthesis of E,E-8,10-dodecadienol, in which a pentenyl derivative is cross-metathesized with 8-nonenol in the presence of Grubbs' catalyst and then treated with an acid or base.

FIG. 12 shows a synthesis of E,E-8,10-dodecadienol, which is the pheromone of the Codling Moth (CM). With reference to FIG. 12, a pentenyl derivative is cross-metathesized with 8-nonenol in the presence of Grubbs' catalyst under vacuum to produce an E-8-dodecenyl derivative with a leaving group designated by X at the E-10 position. Ethylene is removed from the reaction mixture as it is generated. The reaction mixture is then treated with an acid or base to yield E,E-8,10-dodecadienol.

Skilled persons will appreciate that the synthetic schemes shown in FIGS. 9–12 are exemplary only and can be modified by the use of other metathesis catalysts or alcohol-protected protected derivatives of the starting materials as described above with respect to the synthesis of 5-decenyl acetate.

It will be obvious to those having skill in the art that many changes may be made to the details of the above-described embodiment of this invention without departing from the underlying principles thereof. The scope of the present invention should, therefore, be determined only by the following claims.

What is claimed is:

1. A method for synthesizing 5-decenyl acetate, comprising the steps of:
    self-metathesizing 1-hexene in the presence of a first catalyst to form a product;
    cross-metathesizing the product with an alcohol- or acetate-protected hexene or derivative thereof in the presence of a second catalyst to form 5-decenyl acetate or derivative thereof and a side product.

2. The method of claim 1, wherein the first or second catalyst comprises Grubbs' catalyst.

3. The method of claim 1, wherein the first or second catalyst comprises Catalyst 2.

4. The method of claim 1, wherein the product comprises 5-decene.

5. The method of claim 1, further comprising:
    applying vacuum during the step of cross-metathesizing.

6. The method of claim 5 wherein the vacuum has a pressure of less than 50 mm Hg.

7. The method of claim 1, wherein the side product comprises 1-hexene.

8. The method of claim 1, further comprising:
    producing 5-decenyl acetate at a gross yield of greater than 40 percent.

9. The method of claim 8, further comprising:
    producing 5-decenyl acetate at a gross yield of greater than 70 percent.

10. The method of claim 1, further comprising:
    producing 5-decenyl acetate at a trans:cis isomeric ratio of greater than 80:20.

11. The method of claim 1, further comprising:
    producing 5-decenyl acetate at a cost of less than $0.50 per gram.

12. The method of claim 1, further comprising:
producing 5-decenyl acetate in a purity of greater than 95% in a trans:cis isomeric ratio of greater than 80:20 in a time period of less than 100 hours.

13. The method of claim 12, further comprising:
producing 5-decenyl acetate in a time period of less than 25 hours.

14. The method of claim 1, wherein the first or second catalyst comprises:
a catalyst of the structure $[(P)_2AA']Ru=CRR'$, wherein:
L is selected from $—CR_4(R_5)_2$ and cycloalkyl or alkyl-substituted cycloalkyl wherein the number of carbon atoms in the ring is from 4 to 12;
$R_4$ and $R_5$ are each selected from hydrogen and alkyl;
A and A' are anionic ligands independently selected from halogen, hydrogen, $C_1$–$C_{20}$ alkyl, aryl, $C_1$–$C_{20}$ alkoxide, aryloxide, $C_2$–$C_{20}$ alkoxycarbonyl, arylcarboxylate, $C_1$–$C_{20}$ carboxylate, arylsulfonyl, $C_1$–$C_{20}$ alkylsulfonyl, $C_1$–$C_{20}$ alkylsulfinyl, each ligand optionally being substituted with $C_1$–$C_5$ alkyl, halogen, $C_1$–$C_5$ alkoxy or with a phenyl group that is optionally substituted with halogen, $C_1$–$C_5$ alkyl or $C_1$–$C_5$ alkoxy; and
R and R' are independently selected from hydrogen, $C_1$–$C_{20}$ alkyl, aryl, $C_1$–$C_{20}$ carboxylate, $C_1$–$C_{20}$ alkoxy, aryloxy, $C_1$–$C_{20}$ alkoxycarbonyl, $C_1$–$C_{20}$ alkylthio, $C_1$–$C_{20}$ alkylsulfonyl and $C_1$–$C_{20}$ alkylsulfinyl, each of R and R' optionally substituted with $C_1$–$C_5$ alkyl, halogen, $C_1$–$C_5$ alkoxy or with a phenyl group that is optionally substituted with halogen, $C_1$–$C_5$ alkyl or $C_1$–$C_5$ alkoxy.

15. The method of claim 1, wherein the first and second catalysts are the same.

16. The method of claim 1, wherein the acetate-protected hexene comprises 5-hexenoic acid or an ester thereof and wherein the derivative of 5-decenyl acetate is 5-decenoic acid or a salt or ester thereof, the method further comprising:
recrystallizing 5-decenoic acid or a salt or thereof to increase the ratio of trans to cis isomer of 5-decenoic acid or the salt thereof; and
reducing the 5-decenoic acid or the salt or ester thereof to 5-decenol;
acetylating the 5-decenol to produce 5-decenyl acetate having a trans to cis ratio of greater than 90 percent.

17. A method for synthesizing 5-decenyl acetate comprising the steps of:
self-metathesizing 1-hexene in the presence of Grubbs' catalyst to form a mixture of 5-decene and ethylene;
removing the ethylene from the mixture;
cross-metathesizing the 5-decene with a protected hexene having a formula 5-hexene-1-R, where R includes an alcohol, acetate, ether, halide, or ester, in the presence of Grubbs' catalyst to form 1-hexene and 5-decenyl acetate having a trans:cis ratio of greater than 80:20;
performing the cross-metathesizing step under vacuum to remove the 1-hexene as it is formed; and
producing a gross yield of 5-decenyl acetate that is greater than 30 percent.

18. The method of claim 17, wherein the protected hexene is selected from 5-hexen-1-yl acetate or 5-hexen-1-ol.

19. The method of claim 17, wherein the R group is selected from a THP, TMS, or EVE ether, a benzoate or propionate ester, or a chloride, bromide, or iodide halide.

20. A method for synthesizing 5-decenyl acetate, comprising the steps of:
self-metathesizing 5-hexenyl acetate under vacuum and in the presence of a catalyst to form 1,10-diacetoxy-5-decene; and
cross-metathesizing 1,10-diacetoxy-5-decene with 5-decene in the presence of the catalyst to form 5-decenyl acetate.

21. A method for synthesizing olefinic alcohols, acetates, aldehydes, carboxylic acids or derivatives thereof in a reaction chamber, comprising:
self-metathesizing a first alpha olefin in an exemplary form of $CH_2CH(CH_2)_n(CHX)(CH_2)_mCH_3$, where X is selected from a hydrogen, an alcohol, an acetate, a halide, or a tosylate, mesylate or derivative thereof, and n and m are each selected from zero and an integer less than or equal to 20, in the presence of a first catalyst to form a product in the form of $CH_2CH(CH)_p(CHX)(CH_2)_qCH_3$, where p and q are each selected from zero and an integer such that at least p is greater than n or at least q is greater than m and a first side product in the form of $CH_2Y$, where Y is selected from $CH_2$ or $CH(CH_2)_n(CHX)(CH_2)_mCH_3$; and
cross-metathesizing the product with a second alpha olefin in an exemplary form of $NCH(CH_2)_rM$, where N is selected from $CH_2$ or $CH(CH_2)_rM$, r is selected from zero and an integer less than or equal to 20, and M is selected from an alcohol, acetate, aldehyde, halide or carboxylic acid or derivative thereof in the presence of a second catalyst to form a second product in the form of $CH_3(CH_2)_m(CHX)(CH_2)_nCHCH(CH_2)_rM$ or derivatives thereof and a second side product in the form of $CH_2Z$, where Z is selected from $CH_2$ or $CH(CH_2)_n(CHX)(CH_2)_mCH_3$ under conditions of sufficiently high temperature and/or sufficiently low pressure such that the second side product evaporates out of the reaction chamber.

22. The method of claim 21, wherein the first or second catalyst comprise:
a catalyst of the structure $[(PL_3)_2AA']Ru=CRR'$, wherein:
L is selected from $—CR_4(R_5)_2$ and cycloalkyl or alkyl-substituted cycloalkyl wherein the number of carbon atoms in the ring is from 4 to 12;
$R_4$ and $R_5$ are each selected from hydrogen and alkyl;
A and A' are anionic ligands independently selected from halogen, hydrogen, $C_1$–$C_{20}$ alkyl, aryl, $C_1$–$C_{20}$ alkoxide, aryloxide, $C_2$–$C_{20}$ alkoxycarbonyl, arylcarboxylate, $C_1$–$C_{20}$ carboxylate, arylsulfonyl, $C_1$–$C_{20}$ alkylsulfonyl, $C_1$–$C_{20}$ alkylsulfinyl, each ligand optionally being substituted with $C_1$–$C_5$ alkyl, halogen, $C_1$–$C_5$ alkoxy or with a phenyl group that is optionally substituted with halogen, $C_1$–$C_5$ alkyl or $C_1$–$C_5$ alkoxy; and
R and R' are independently selected from hydrogen, $C_1$–$C_{20}$ alkyl, aryl, $C_1$–$C_{20}$ carboxylate, $C_1$–$C_{20}$ alkoxy, aryloxy, $C_1$–$C_{20}$ alkoxycarbonyl, $C_1$–$C_{20}$ alkylthio, $C_1$–$C_{20}$ alkylsulfonyl and $C_1$–$C_{20}$ alkylsulfinyl, each of R and R' optionally substituted with $C_1$–$C_5$ alkyl, halogen, $C_1$–$C_5$ alkoxy or with a phenyl group that is optionally substituted with halogen, $C_1$–$C_5$ alkyl or $C_1$–$C_5$ alkoxy.

23. The method of claim 21, wherein the step of self metathesizing is performed under conditions of sufficiently high temperature and/or sufficiently low pressure such that the first side product evaporates out of the reaction chamber.

24. The method of claim 21, wherein the first product is 5-decene or 5-decenoic acid or a salt or ester thereof.

25. The method of claim 24, wherein the second product is 5-decenyl acetate or an acid, salt, or ester thereof.

26. The method of claim 21, wherein the first and/or second catalyst comprises Grubbs' catalyst or Catalyst 2.

* * * * *